(12) United States Patent
Parikh et al.

(10) Patent No.: US 11,439,760 B2
(45) Date of Patent: Sep. 13, 2022

(54) SYRINGES

(71) Applicants: Nilesh Parikh, Irvine, CA (US);
William Hite, Winchester, CA (US)

(72) Inventors: Nilesh Parikh, Irvine, CA (US);
William Hite, Winchester, CA (US)

( * ) Notice: Subject to any disclaimer, the term of this patent is extended or adjusted under 35 U.S.C. 154(b) by 127 days.

(21) Appl. No.: 16/510,955

(22) Filed: Jul. 14, 2019

(65) Prior Publication Data
US 2021/0008291 A1    Jan. 14, 2021

(51) Int. Cl.
*A61M 5/315* (2006.01)
*A61M 5/31* (2006.01)
*A61M 5/14* (2006.01)
*G09F 3/02* (2006.01)
*A61M 5/28* (2006.01)
*A61M 5/00* (2006.01)

(52) U.S. Cl.
CPC ...... *A61M 5/31525* (2013.01); *A61M 5/1412* (2013.01); *A61M 5/3129* (2013.01); *A61M 5/002* (2013.01); *A61M 5/28* (2013.01); *A61M 2005/3126* (2013.01); *G09F 2003/0272* (2013.01)

(58) Field of Classification Search
CPC ............ A61M 5/31525; A61M 5/1412; A61M 5/3129; A61M 5/002; A61M 5/28; A61M 2005/3126; G09F 2003/0272
See application file for complete search history.

(56) References Cited

U.S. PATENT DOCUMENTS

| | | | |
|---|---|---|---|
| 2,432,605 | A | 12/1947 | Barach |
| 6,338,200 | B1 | 1/2002 | Boxa |
| 9,192,723 | B2 | 11/2015 | Creaturo |
| 9,302,050 | B2 | 4/2016 | Creaturo |
| 2002/0087121 | A1 | 4/2002 | Slishman |
| 2015/0231335 | A1 | 8/2015 | Creaturo |

(Continued)

FOREIGN PATENT DOCUMENTS

| | | |
|---|---|---|
| WO | 2019108467 | 6/2019 |
| WO | 2021011508 | 1/2021 |

OTHER PUBLICATIONS

PCT_International_Preliminary_Report_on_Patentability_PCTUS2020041866.
PCT_Written_Opinion_of_the_International_Searching_Authority_PCTUS2020041866.
PCT_International_Search_Report_PCTUS2020041866.

*Primary Examiner* — Lauren P Farrar

(57) ABSTRACT

Embodiments of this invention provide syringes calibrated for use with a predetermined liquid medication having an active pharmaceutical ingredient (API) at a particular weight per unit volume (w/v) concentration. Such syringes comprising a plunger and a barrel are configured such that the plunger, and/or an end portion of the plunger, is sealingly receivable through an opening at one end the barrel and within the barrel and slidingly moveable lengthwise within the barrel. This configuration allows formation of a reservoir inside the barrel into which the liquid medication may be loaded through an intake opening for the liquid medication at the other end of the barrel. Syringe barrels according to this invention possess line increments that form two or more graduated scales of API weight dosages extending lengthwise along the barrels. The increment lines provide for highly precise and accurate measurement of fine-increment weight dosages of the API.

17 Claims, 6 Drawing Sheets

(56) References Cited

U.S. PATENT DOCUMENTS

| | | |
|---|---|---|
| 2016/0166774 A1 | 6/2016 | Leary |
| 2016/0166776 A1 | 6/2016 | Appelbaum |
| 2019/0351144 A1* | 11/2019 | Hernandez ............ A61M 5/178 |
| 2020/0254186 A1 | 8/2020 | Hernandez |
| 2020/0261655 A1* | 8/2020 | Appelbaum ........... B65D 25/36 |

* cited by examiner

SYRINGES

FIELD OF THE INVENTION

The present invention relates to syringes configured for easy and accurate administration to a patient of very precisely measured dosages of a liquid medication having a predetermined concentration of active pharmaceutical ingredient ("API").

BACKGROUND OF THE INVENTION

Syringes are widely used for the measurement and administration of liquid medications. For a variety of reasons, incorrect dosing of liquid medications administered with syringes is a common problem that leads to serious consequences associated with under/overdosing the liquid medication. This problem arises from several factors, common among them errors in API dose calculation and/or measurement of liquid medication volume.

For instance, the strengths or concentrations of liquid medications are typically labeled in weight to volume units, such as milligrams of API per milliliter of a medication (mg/ml) or micrograms of API per milliliter of a medication (µg/ml). On the other hand, the required dose of a liquid medication to be administered is often given in milligrams or micrograms of API per kilogram of patient body weight, respectively, (mg/kg) car (µg/kg). Yet almost all commercially available syringes have a barrel marked only with volumetric graduations. So a health care provider or the patient (if self-administering a medication) must perform a calculation to determine the volume of liquidation medication that must be drawn into the barrel of such syringes, to load a desired weight-dosage of API (e.g., mg or mcg) for administration to the patient.

These calculations include multiplying the patient's body weight by the weight scale dosing of API (in mg/kg of patient body weight or mcg/kg of patient body weight), which yields the target weight dose of API (e.g., mg or mcg) to be administered to the patient. That target weight dose of API (e.g., mg or mcg) then must be divided by the concentration of the liquid medication (e.g., mg or µg of API per ml of the liquid medication) to determine the required volume to be drawn into the syringe barrel for administration to the patient.

Such complexities associated with administering liquid medications by syringe give rise to risk of incorrect dosing of liquid medication, even under the best of circumstances. The risk increases under more challenging circumstances, such as a medically distressed patient or an inexperienced caregiver. As mentioned above, inaccurate dosing of liquid medication gives rise to risk of adverse effects caused by under/overdose for any API. And such risks are particularly acute in the context of administration of an API having a narrow therapeutic index.

SUMMARY OF THE INVENTION

Accordingly, there is a need for a syringe configured to administer liquid medications in a manner that avoids the aforementioned complex and error-prone calculations which give rise to material risks of under/overdosing. U.S. Pat. No. 9,302,050 (the "'050 patent") discloses syringes configured, in a complicated manner, for use with predetermined liquid medications: i.e., they comprise two or more columns of graduated markings on their barrel that indicate two or more of the following: (a) patient characteristics (i.e., body weight or body surface area): (b) liquid medication volume; and (c) API weight or units. The syringes taught by the '050 patent further comprise, on their plungers, information about the predetermined liquid medication volume or API weight).

FIG. 1 herein reproduces FIG. 1 of the '050 patent, aside from the omission of its numbering. It shows that barrel markings of syringes taught by the '050 patent comprise two to four columns of tightly spaced markings that form graduated scales indicating: (i) patient weight values (labeled in kg); (ii) liquid medication volume values (labeled in mL); and (iii) liquid medication API weight values (labeled in mg). FIG. 1 further shows that accent bar markings in graduated scales connect two or more of the graduated scale columns specified in (i)-(iii). The net effect of the dense, complex, and interconnected arrangement of syringe barrel markings taught by the '050 patent is to make them confusingly busy and difficult to read, interpret, and use. Such arrangement gives rise to material risk of a patient or caregiver drawing an incorrect amount of liquid into the barrel of the syringe; and therefore under/overdosing the administered liquid medication.

Further still, select characteristics of the liquid medication (e.g., API identity and strength) to be administered by a syringe taught by the '050 patent are printed on the plunger, together with the scale for API weight dosage to patient body weight. (See FIG. 2, which reproduces FIG. 5 of the '050 patent except for the omission of numbering.) The scale on the plunger provides information redundant to that provided by markings of the syringe barrel; but confusingly expressed in a different format than that on the barrel. This arrangement raises risk of confusion in a user of the syringe regarding whether the scale and related barrel markings indicate the same or different information and whether the syringe and plunger are indeed intended to be used together. (See FIG. 2.) These circumstances further exacerbate the difficulties mentioned above with respect to reading, interpreting, and using syringes taught by the '050 patent.

Embodiments. Embodiments of the present invention provide syringes possessing on their barrels two or more easy-to-read graduated scales indicating fine-increment, weight dosages of the API in the liquid medication. Each of the spacing, arrangement, and design of the line increments of the graduated scales indicating API weight dosages; the volumetric dimensions of the syringe barrel; and the API strength of the liquid medication (i.e., API weight per unit volume) are coordinately configured to effectively achieve highly accurate and highly precise measurement and administration of fine-increment, API weight dosages of a predetermined liquid medication. Reference numbers recited in below embodiments 1-31 refer to the drawings illustrated in FIGS. 3, 4, 5, and 6.

Embodiment 1: A syringe 1, calibrated for use with a predetermined liquid medication having a particular active pharmaceutical ingredient (API) at a particular weight per unit volume (w/v) concentration. The syringe comprises a plunger 20 and a barrel 10. One end of the barrel comprises and opening 22 for the plunger and the other end comprises an intake opening 17 for the liquid medication. The plunger and the barrel are configured such that the plunger, or an end portion 25 of the plunger, is sealingly receivable through the plunger opening at one end the barrel and within the barrel and also slidingly moveable lengthwise within the barrel. This configuration forms a volumetrically adjustable reservoir 15 inside the barrel into which the liquid medication may be loaded through the intake opening for the liquid medication at the other end of the barrel. In such a syringe, the barrel is made, in whole or in part, from substantially transparent material through which liquid medication inside the reservoir is visible. The barrel comprises, extending along its lengthwise axis, two or more graduated scales 30, 40, 50 of liquid medication API weight dosages on the substantially transparent material of the barrel, each of the two or more graduated scales occupying non-overlapping arcs running lengthwise along the circumference of the barrel. Each graduated scale is formed of a plurality of increment API weight dosage lines 60 for the liquid medication, each increment line running perpendicular to the lengthwise axis of the barrel and each immediately adjacent increment line of any one graduated scale indicating API weight dosages that differ from each other by no more than 100 mg. The increment lines of one graduated scale are offset, along the lengthwise axis of the barrel, from increment lines of all the other graduated scales. At least every fifth increment line of one graduated scale is labeled with the numerical value of the weight dosage of the API indicated thereby. And the API of the predetermined liquid medication possesses a narrow therapeutic index.

Embodiment 2: A syringe 1, calibrated for use with a predetermined liquid medication having a particular active pharmaceutical ingredient (API) at a particular weight per unit volume (w/v) concentration. The syringe comprises a plunger 20 and a barrel 10. One end of the barrel comprises and opening 22 for the plunger and the other end comprises an intake opening 17 for the liquid medication. The plunger and the barrel are configured such that the plunger, or an end portion 25 of the plunger, is sealingly receivable through the plunger opening at one end the barrel and within the barrel and also slidingly moveable lengthwise within the barrel. This configuration forms a volumetrically adjustable reservoir 15 inside the barrel into which the liquid medication may be loaded through the intake opening for the liquid medication at the other end of the barrel. In such a syringe, the barrel is made, in whole or in part, from substantially transparent material through which liquid medication inside the reservoir is visible. The barrel comprises, extending along its lengthwise axis, two or more graduated scales 30, 40, 50 of liquid medication API weight dosages on the substantially transparent material of the barrel, each of the two or more graduated scales occupying non-overlapping arcs running lengthwise along the circumference of the barrel. Each graduated scale is formed of a plurality of increment API weight dosage lines 60 for the liquid medication, each increment line running perpendicular to the lengthwise axis of the barrel and each immediately adjacent increment line of any one graduated scale indicating API weight dosages that differ from each other by no more than 100 μg. The increment lines of one graduated scale are offset, along the lengthwise axis of the barrel, from increment lines of all the other graduated scales. At least every fifth increment line of one graduated scale is labeled with the numerical value of the weight dosage of the API indicated thereby. And the API of the predetermined liquid medication possesses a narrow therapeutic index.

Embodiment 3: A syringe 1, calibrated for use with a predetermined liquid medication having a particular active pharmaceutical ingredient (API) at a particular weight per unit volume (w/v) concentration. The syringe comprises a plunger 20 and a barrel 10. One end of the barrel comprises and opening 22 for the plunger and the other end comprises an intake opening 17 for the liquid medication. The plunger and the barrel are configured such that the plunger, or an end portion 25 of the plunger, is sealingly receivable through the plunger opening at one end the barrel and within the barrel and also slidingly moveable lengthwise within the barrel. This configuration forms a volumetrically adjustable reservoir 15 inside the barrel into which the liquid medication may be loaded through the intake opening for the liquid medication at the other end of the barrel. In such a syringe, the barrel is made, in whole or in part, from substantially transparent material through which liquid medication inside the reservoir is visible. The barrel comprises, extending along its lengthwise axis, two or more graduated scales 30, 40, 50 of liquid medication API weight dosages on the substantially transparent material of the barrel, each of the two or more graduated scales occupying non-overlapping arcs running lengthwise along the circumference of the barrel. Each graduated scale is formed of a plurality of increment API weight dosage lines 60 for the liquid medication, each increment line running perpendicular to the lengthwise axis of the barrel and each immediately adjacent increment line of any one graduated scale indicating API weight dosages that differ from each other by no more than 100 ng. The increment lines of one graduated scale are offset, along the lengthwise axis of the barrel, from increment lines of all the other graduated scales. At least every fifth increment line of one graduated scale is labeled with the numerical value of the weight dosage of the API indicated thereby. And the API of the predetermined liquid medication possesses a narrow therapeutic index.

Embodiment 4: A syringe 1, calibrated for use with a predetermined liquid medication having a particular active pharmaceutical ingredient (API) at a particular weight per unit volume (w/v) concentration. The syringe comprises a plunger 20 and a barrel 10. One end of the barrel comprises and opening 22 for the plunger and the other end comprises an intake opening 17 for the liquid medication. The plunger and the barrel are configured such that the plunger, or an end portion 25 of the plunger, is sealingly receivable through the plunger opening at one end the barrel and within the barrel and also slidingly moveable lengthwise within the barrel. This configuration forms a volumetrically adjustable reservoir 15 inside the barrel into which the liquid medication may be loaded through the intake opening for the liquid medication at the other end of the barrel. In such a syringe, the barrel is made, in whole or in part, from substantially transparent material through which liquid medication inside the reservoir is visible. The barrel comprises, extending along its lengthwise axis, two or more graduated scales 30, 40, 50 of liquid medication API weight dosages on the substantially transparent material of the barrel, each of the two or more graduated scales occupying non-overlapping arcs running lengthwise along the circumference of the barrel. Each graduated scale is formed of a plurality of increment API weight dosage lines 60 for the liquid medication, each increment line running perpendicular to the lengthwise axis of the barrel and each immediately adjacent increment line of any one graduated scale indicating API weight dosages that differ from each other by no more than 100 pg. The increment lines of one graduated scale are offset, along the lengthwise axis of the barrel, from increment lines of all the other graduated scales. At least every fifth increment line of one graduated scale is labeled with the numerical value of the weight dosage of the API indicated thereby. And the API of the predetermined liquid medication possesses a narrow therapeutic index.

Embodiment 5: A syringe 1, calibrated for use with a predetermined liquid medication having a particular active pharmaceutical ingredient (API) at a particular weight per unit volume (w/v) concentration. The syringe comprises a plunger 20 and a barrel 10. One end of the barrel comprises and opening 22 for the plunger and the other end comprises an intake opening 17 for the liquid medication. The plunger and the barrel are configured such that the plunger, or an end portion 25 of the plunger, is sealingly receivable through the plunger opening at one end the barrel and within the barrel and also slidingly moveable lengthwise within the barrel. This configuration forms a volumetrically adjustable reservoir 15 inside the barrel into which the liquid medication may be loaded through the intake opening for the liquid medication at the other end of the barrel. In such a syringe, the barrel is made, in whole or in part, from substantially transparent material through which liquid medication inside the reservoir is visible. The barrel comprises, extending along its lengthwise axis, two or more graduated scales 30, 40, 50 of liquid medication API weight dosages on the substantially transparent material of the barrel, each of the two or more graduated scales occupying non-overlapping arcs running lengthwise along the circumference of the barrel. Each graduated scale is formed of a plurality of increment API weight dosage lines 60 for the liquid medication, each increment line running perpendicular to the lengthwise axis of the barrel and each immediately adjacent increment line of any one graduated scale indicating API weight dosages that differ from each other by no more than 100 fg. The increment lines of one graduated scale are offset, along the lengthwise axis of the barrel, from increment lines of all the other graduated scales. At least every fifth increment line of one graduated scale is labeled with the numerical value of the weight dosage of the API indicated thereby. And the API of the predetermined liquid medication possesses a narrow therapeutic index Embodiment 6: The syringe of embodiment 1, wherein each immediately adjacent increment line of any one graduated scale indicate API weight dosages that differ from each other by no more than 90 mg, 80 mg, 70 mg, 60 mg, 50 mg, 40 mg, 30 mg, 20 mg, 15 mg, 10 mg, or 5 mg.

Embodiment 7: The syringe of either one of embodiments 1 or 6, wherein the syringe is calibrated for use with the predetermined liquid medication having the particular API w/v concentration that falls in a range of 1 mg/ml to 999 mg/ml.

Embodiment 8: The syringe of any one of embodiments 1, 6, or 7, wherein the collection of increment lines of all the graduated scales are all arranged on the barrel in a manner such that, moving in a spiral fashion along the lengthwise axis of the barrel from any one increment line of a first graduated scale to another increment line of a second graduated scale that is closest in proximity to the one increment line, the one and the another increment lines indicate API weight dosages that differ from each other by no more than 50 mg, 40 mg, 30 mg, 20 mg, 15 mg, 10 mg, or 5 mg.

Embodiment 9: The syringe of embodiment 2, wherein each immediately adjacent increment line of any one graduated scale indicate API weight dosages that differ from each other by no more than 90 μg, 80 μg, 70 μg, 60 μg, 50 μg, 40 μg, 30 μg, 20 μg, 15 μg, 10 μg, or 5 μg.

Embodiment 10: The syringe either one of embodiments 2 or 9, wherein the syringe is calibrated for use with the predetermined liquid medication having the particular API w/v concentration that falls in a range of 1 μg/ml to 999 μg/ml.

Embodiment 11: The syringe of any one of embodiments 2, 9, or 10, wherein the collection of increment lines of all the graduated scales are all arranged on the barrel in a manner such that, moving in a spiral fashion lengthwise along the barrel from any one increment line of a first graduated scale to another increment line of a second graduated scale that is closest in proximity to the one increment line, the one and the another increment lines indicate API weight dosages that differ from each other by no more than 50 μg, 40 μg, 30 μg, 20 μg, 15 μg, 10 μg, or 5 μg.

Embodiment 12: The syringe of embodiment 3, wherein each immediately adjacent increment line of any one graduated scale indicate API weight dosages that differ from each other by no more than 90 ng, 80 ng, 70 ng, 60 ng, 50 ng, 40 ng, 30 ng, 20 ng, 15 ng, 10 ng, or 5 ng.

Embodiment 13: Embodiment 10: The syringe either one of embodiments 3 or 12, wherein the syringe is calibrated for use with the predetermined liquid medication having the particular API w/v concentration that falls in a range of 1 ng/ml to 999 ng/ml.

Embodiment 14: The syringe of any one of embodiments 3, 12, or 13, wherein the collection of increment lines of all the graduated scales are all arranged on the barrel in a manner such that, moving in a spiral fashion lengthwise along the barrel from any one increment line of a first graduated scale to another increment line of a second graduated scale that is closest in proximity to the one increment line, the one and the another increment lines indicate API weight dosages that differ from each other by no more than 50 ng, 40 ng, 30 ng, 20 ng, 15 ng, 10 ng, or 5 ng.

Embodiment 15: The syringe of embodiment 4, wherein each immediately adjacent increment line of any one graduated scale indicate API weight dosages that differ from each other by no more than 90 pg, 80 pg, 70 pg, 60 pg, 50 pg, 40 pg, 30 pg, 20 pg, 15 pg, 10 pg, or 5 pg.

Embodiment 16: The syringe of either one of embodiments 4 or 15, wherein the syringe is calibrated for use with the predetermined liquid medication having the particular API w/v concentration that falls in a range of 1 pg/ml to 999 pg/ml.

Embodiment 17: The syringe of any one of embodiment 4, 15, or 16, wherein the collection of increment lines of all the graduated scales are all arranged on the barrel in a manner such that, moving in a spiral fashion lengthwise along the barrel from any one increment line of a first graduated scale to another increment line of a second graduated scale that is closest in proximity to the one increment line, the one and the another increment lines indicate API weight dosages that differ from each other by no more than 50 pg, 40 pg, 30 pg, 20 pg, 15 pg, 10 pg, or 5 pg.

Embodiment 18: The syringe of embodiment 5, wherein each immediately adjacent increment line of any one graduated scale indicate API weight dosages that differ from each other by no more than 90 fg, 80 fg, 70 fg, 60 fg, 50 fg, 40 fg, 30 fg, 20 fg, 15 fg, 10 fg, or 5 fg.

Embodiment 19: The syringe of either one of embodiments 5 or 18, wherein the syringe is calibrated for use with the predetermined liquid medication having the particular API w/v concentration that falls in a range of 1 fg/ml to 999 fg/ml.

Embodiment 20: The syringe of any one of embodiments 5, 18, or 19, wherein the collection of increment lines of all the graduated scales are all arranged on the barrel in a manner such that, moving in a spiral fashion lengthwise along the barrel from any one increment line of a first graduated scale to another increment line of a second graduated scale that is closest in proximity to the one increment line, the one and the another increment lines indicate API weight dosages that differ from each other by no more than 50 fg, 40 fg, 30 fg, 20 fg, 15 fg, 10 fg, or 5 fg.

Embodiment 21: The syringe of any one of embodiments 1 through 20, wherein a maximum API weight dosage indicated by a graduated scale corresponds to a volume of the liquid medication loaded into the reservoir that is 1 ml, 2 ml, 3 ml, 5 ml, 10 ml, 15 mL, 20 ml, 25 ml, or 50 ml.

Embodiment 22: The syringe of any one of embodiments 1 through 21, wherein each increment line is printed, stamped, embossed, engraved, and/or etched onto the barrel.

Embodiment 23: The syringe of any one of embodiments 1 through 22, wherein the barrel further comprises the name of the API in printed, stamped, embossed, and/or etched lettering.

Embodiment 24: The syringe of any one of embodiments 1 through 23, wherein each immediately adjacent increment line, of any one graduated scale, indicates API weight dosages that differ from each other by a constant amount or by a substantially constant amount. As used herein, the term "substantially constant amount" means, with regards to increment lines of graduated scales of API weight dosages, that all immediately adjacent increment lines of any one graduated scale indicate API weight dosages that differ from each other by no more than 50, 40, 30, 20, 10, 5, or 1 milligram(s), microgram(s), nanogram(s), picogram(s), or femtogram(s), as applicable.

Embodiment 25: The syringe of any one of embodiments 1 through 24, wherein the API has a narrow therapeutic index.

Embodiment 26: The syringe of any one of embodiments 1 through 25, wherein there are three, four, or five graduated scales on the barrel Embodiment 27: The syringe of any one of embodiments 2, 9, 10, or 11, wherein the API is levothyroxine or a pharmaceutically acceptable salt thereof.

Embodiment 28: The syringe of embodiment 27, wherein the maximum API weight dosage indicated by any graduated scale corresponds to a volume of the liquid medication loaded into the reservoir that is 3 ml or 5 ml.

Embodiment 29: The syringe of embodiment 28, wherein the syringe is calibrated for use with the predetermined liquid medication having the particular API w/v concentration that is 30 μg/ml or 50 μg/ml of levothyroxine.

Embodiment 30: The syringe of embodiment 29, wherein there are three graduated scales on the barrel.

Embodiment 31: The syringe of embodiment 31, wherein the collection of increment lines of all the graduated scales are all arranged on the barrel in a manner such that, moving in a spiral fashion up the barrel of the syringe from any one increment line of a first graduated scale to another increment line of a second graduated scale that is closest in proximity to the one increment line, the one and the another increment lines indicate API weight dosages that differ from each other by no more than 5 μg. (One might visualize the arrangement of such line increments, for a syringe having three graduated scales, as being illustrated in FIG. 3 wrapped around a syringe barrel.)

Embodiment 32: The syringe of any one of embodiments 1 through 31, wherein graduation scales separation marking 55 separate one graduation scale from another. (See, e.g. the vertical lines in FIG. 3)

DETAILED DESCRIPTION OF THE INVENTION

Figure 1:
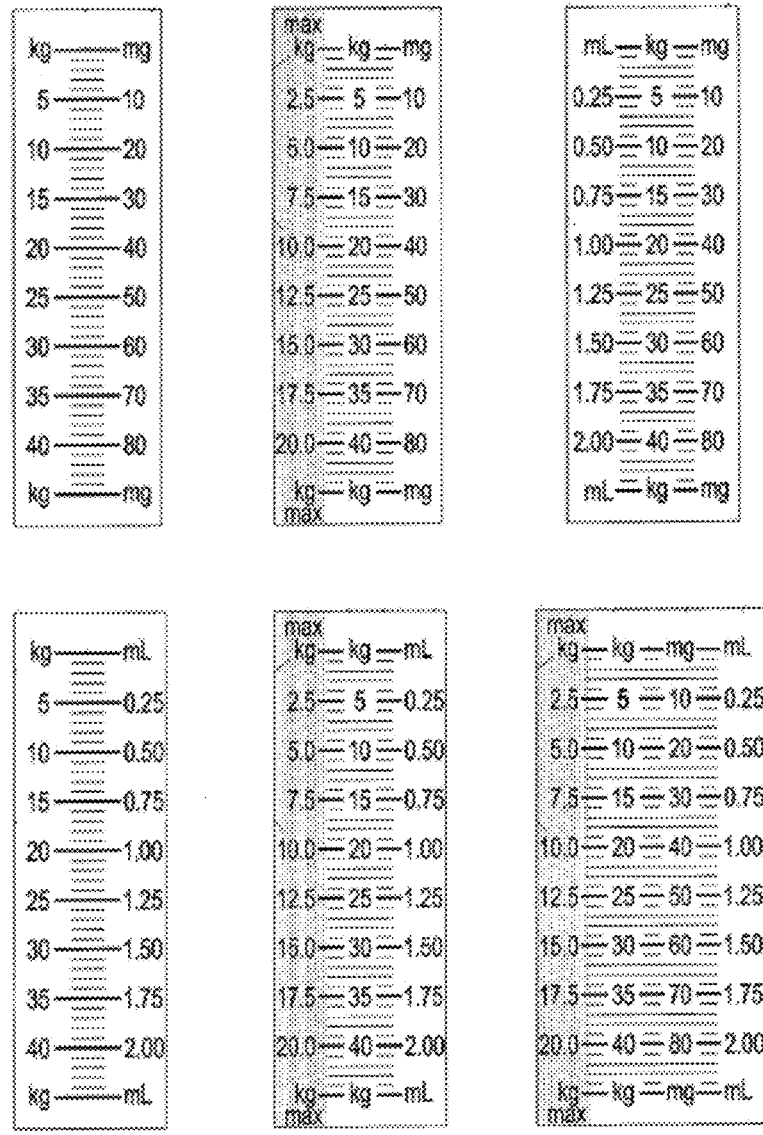
FIG. 1 shows a flat view of a syringe barrel according to U.S. Pat. No. 9,302,050.
Figure 2:
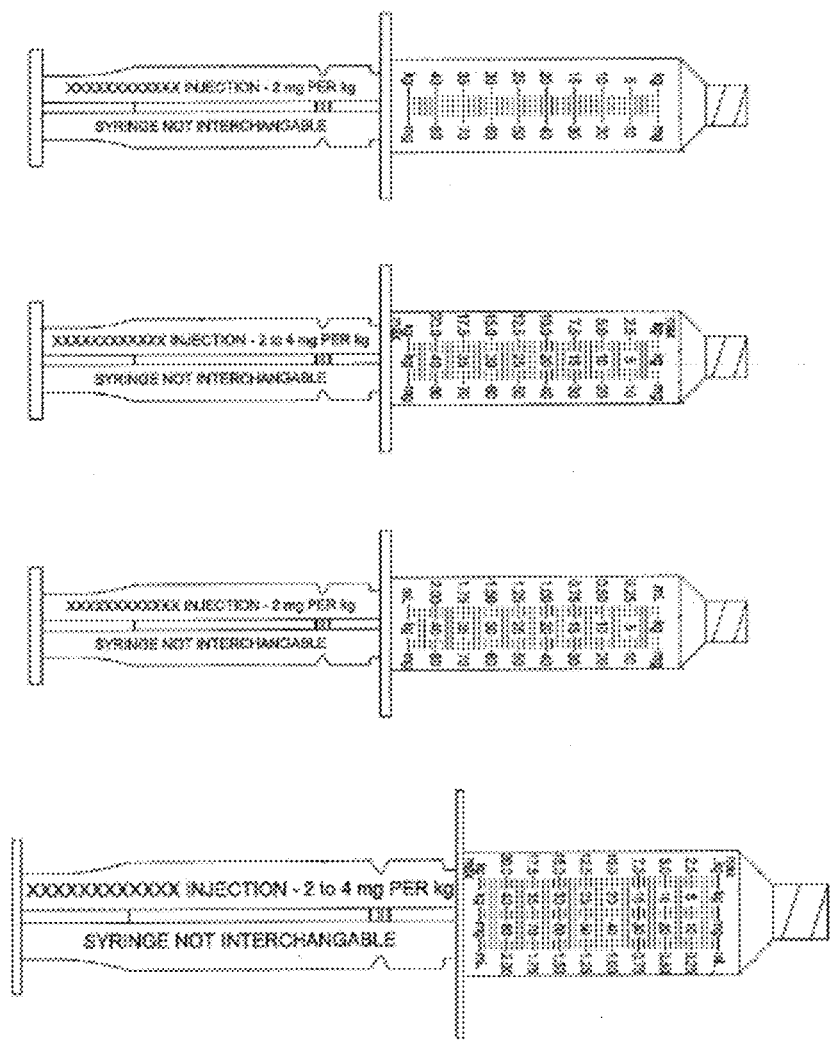
FIG. 2 shows side views of syringe barrels and plungers according to U.S. Pat. No. 9,302,050
Figure 3:
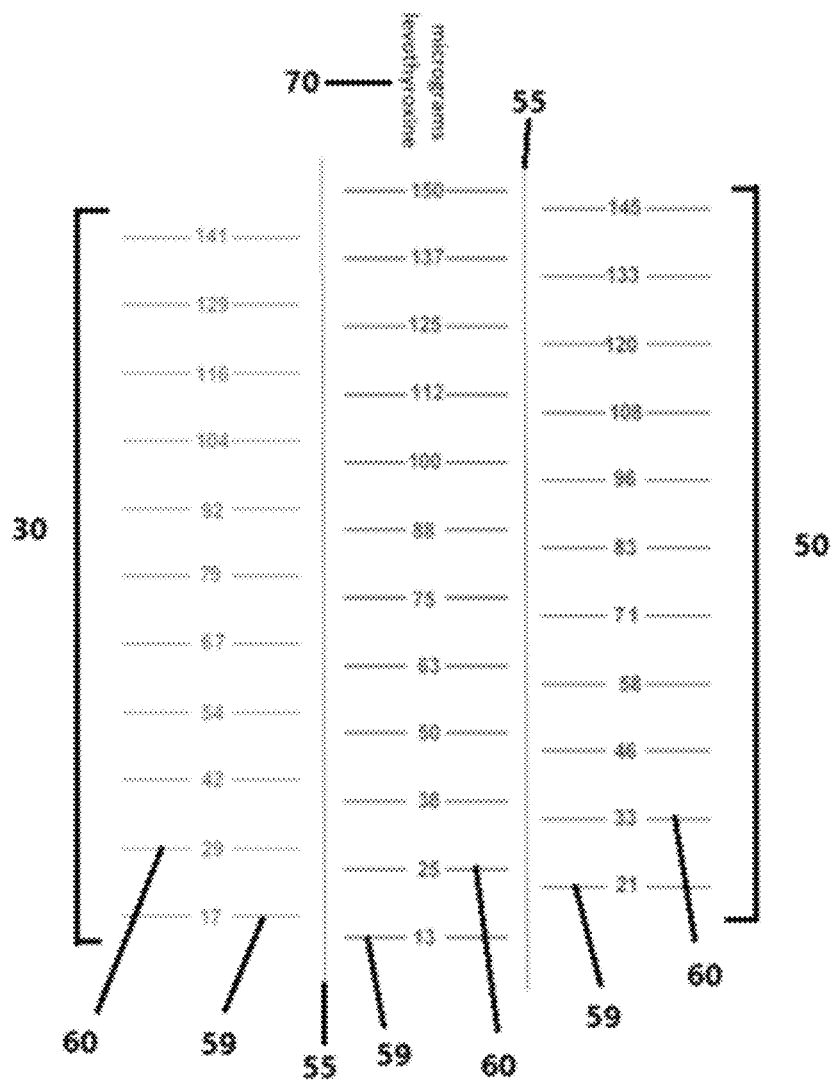
FIG. 3 shows a flat view of a syringe barrel according to the present disclosure.

The present invention will now be described more fully with reference to the drawings in which exemplary embodiments of the invention are shown. However, the invention may be embodied in many different forms and should not be construed as limited to the exemplary embodiments set forth in the drawings or to otherwise described details thereof. Rather, departures may be made from such exemplary embodiments and still fall within the scope of the present invention. Like reference numbers in the drawings refer to like elements of syringes throughout the drawings of exemplary embodiments of the invention.

Figure 4:
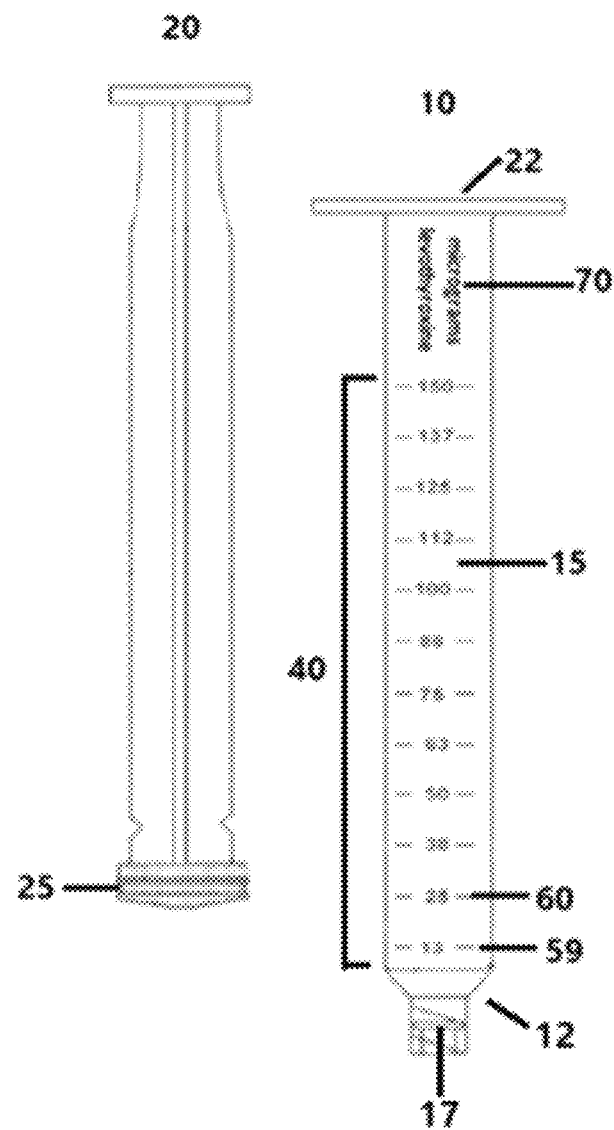
FIG. 4 shows a first side view of the syringe barrel of FIG. 3, together with a plunger.
Figure 5:
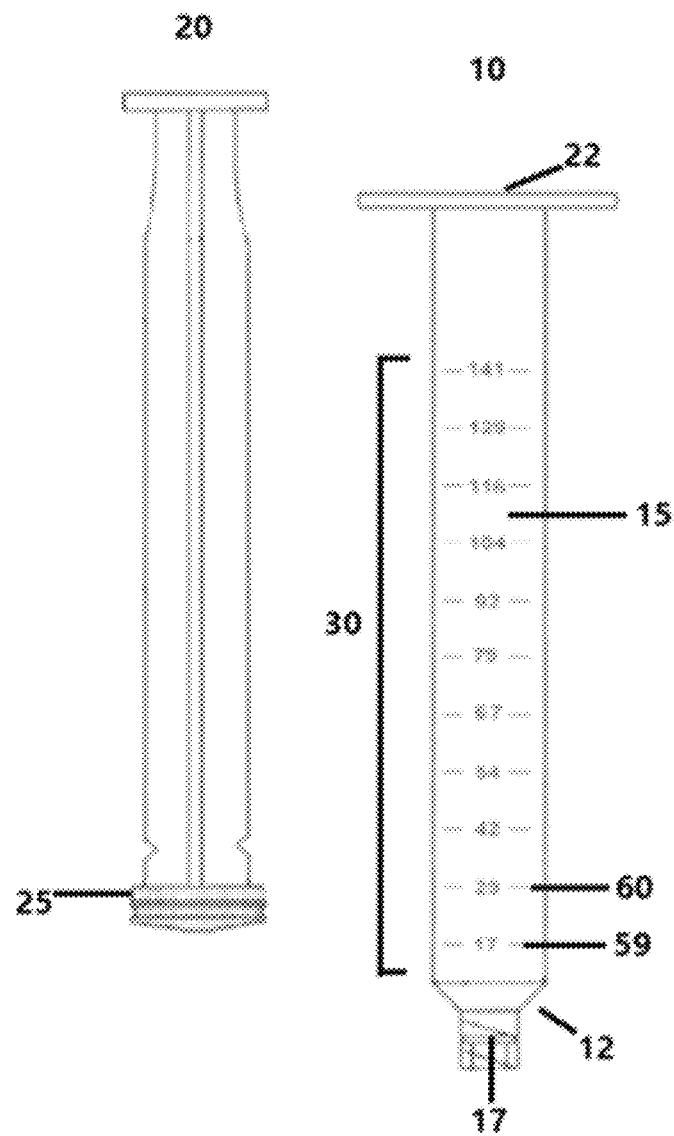
FIG. 5 shows a second side view of the syringe barrel of FIG. 3, together with a plunger.
Figure 6:
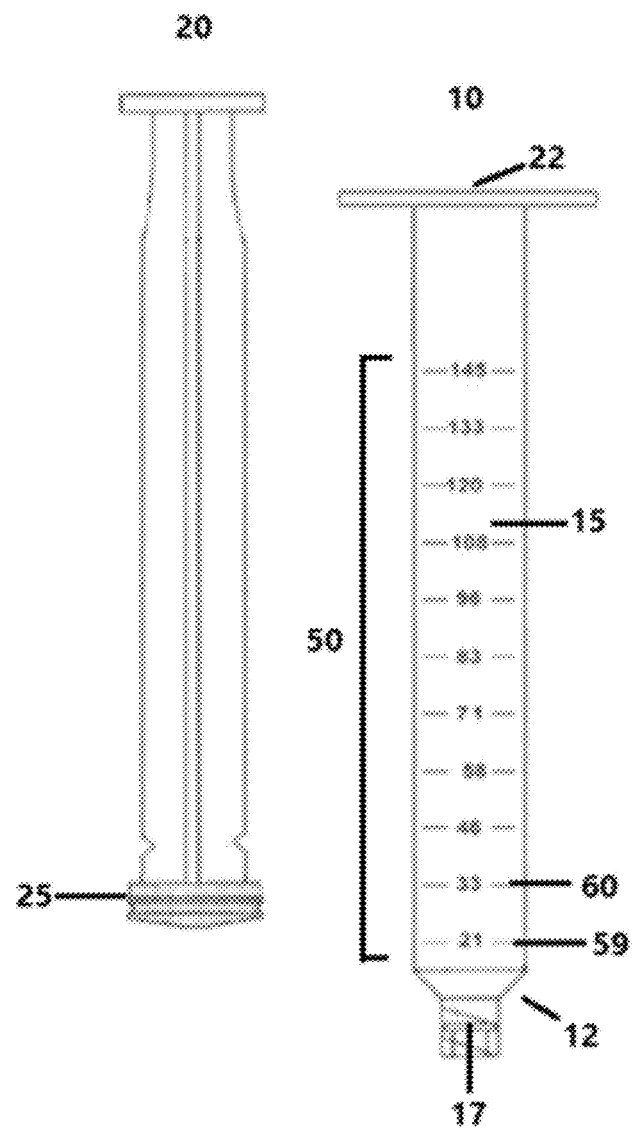
FIG. 6 shows a third side view of the syringe barrel of FIG. 3, together with a plunger.

Referring to FIGS. 4-6, syringe 1 according to the present disclosure is adapted for easy and accurate administration to a patient (without a needle for administering orally or topically, or with a needle for administering by injection to any suitable body site (not shown)) of very accurate and precise API weight dosages of a predetermined liquid medication. Such syringes comprise a barrel 10 having a reservoir 15 and a tip 12 with an intake opening 17 at one end of the reservoir and a plunger 20 that may have an end portion 25. The barrel and plunger are configured such that the plunger, and/or its end portion, is/are: (i) sealingly receivable by open end 22 of the barrel and within the barrel, and (ii) axially moveable within the barrel, which configuration renders the syringe operable to draw liquid medication into the reservoir through the opening of the tip.

Syringe barrels 10 of the present disclosure possess easy to read increment lines of API weight dosages 59, 60 that form graduated scales of API weight dosages 30, 40, 50 extending axially along two or more sides of the syringe barrel. (FIGS. 3-6.) Further, syringe barrels of the present disclosure are made, in whole or in part, from substantially transparent material that enables a user of the syringe to readily see the content the syringe barrel reservoir 15. Increment lines 59, 60 forming graduated scales of API weight dosages appear, in whole or in part, on the substantially transparent portions of the syringe barrel. (FIGS. 4-6.) In certain embodiments, syringe barrels according to the present disclosure possess easy to read indicia of the name or other indication of the identity of the API 70 of the predetermined medication to be administered with the syringe. (FIGS. 3-6.)

At least the following characteristics of syringes according to the present disclosure are coordinately calibrated to achieve the facile and highly precise and highly accurate measurement of fine-increment, API weight dosages for the predetermined liquid medications to be used therewith: (i) the weight per volume API concentration of said predetermined liquid medication; (ii) the lengthwise axial spacing of the increment lines of the API weight dosage graduated scales; (iii) the diameter of the syringe barrel; and (iv) volumetric capacity of the reservoir within the syringe barrel.

In operation, a user places an intake opening 17 of a syringe according to the present invention in fluid communication with a source of the predetermined liquid medication, with the plunger positioned at its lengthwise limit deep inside the barrel of the syringe such that, as the user pulls the plunger away from the intake opening, the liquid medication is drawn into the reservoir of the barrel. A user loads a particular, intended API weight dosage of the liquid medication into the reservoir of the barrel by aligning, with the syringe barrel in a vertical (or nearly vertical) position, the bottom of a surface meniscus of said liquid medication drawn into the barrel reservoir with an individual increment line of a graduated scale that corresponds to the API weight dosage intended for administration.

The increment lines 59, 60 of the graduated scales 30, 40, 50 on syringe barrels 10 of the instant invention are arrayed as follows. The individual line increments 59, 60 of a first graduated scale of API weight dosages 40 that is closest to the intake opening 17 of the syringe is indicative of the smallest API weight dosage of predetermined liquid medication that may be loaded into the barrel reservoir 15, and administered by, the syringe 1. Starting from this increment line and spiraling upward from the intake opening around the circumference of the syringe barrel 10 in one direction (for example, in reference to FIG. 3, leftward as one goes up the barrel from the tip), each subsequently encountered increment line of a graduated scale of API weight dosages that is both: (i) closest in proximity to the last increment line, and (ii) further up the barrel 10 away from the intake opening 17 of the syringe is indicative of the next largest API weight dosage of predetermined liquid medication that may be loaded into, and administered by, the syringe 1. (FIGS. 3-6.)

This configuration provides sufficient spacing between increment lines within each of the graduated scales of API weight dosages to render them easily and accurately readable by the user. Simultaneously, this configuration allows for the increment lines among the different graduated scales of API weight dosages present on the syringe barrel to be easily distinguished from one another and provides easy and accurate loading of highly precise and highly accurate, fine-increment API weight dosages of the predetermined liquid medication by the syringe.

Syringes according to the present disclosure are uniquely suitable for administration of narrow therapeutic index APIs. The therapeutic index (TI) of an API is the range of doses at which the API demonstrates therapeutic efficacy and does not cause adverse events. APIs with narrow TI have a narrow window between their therapeutically effective dosages and dosage at which they produce adverse toxic effects. In order to achieve therapeutic efficacy with narrow TI APIs, while avoiding under-dosing (lack of therapeutic effect) and over-dosing (causation of adverse events), administration of such APIs should typically be initially carefully titrated for clinical response between fine-increment dosages that are accurately and precisely administered. Upon identification of the appropriate API dosage for achieving therapeutic effect, that dose should be accurately administered on a continuing basis. It follows that the easy and highly precise and highly accurate loading and administration of fine-increment API weight dosages at of predetermined liquid medications by the syringe disclosed herein make these syringes uniquely suitable for use with narrow TI APIs.

Non-limiting examples of narrow TI APIs include aminoglycosides, cyclosporine, carbamazepine, digoxin, digitoxin, flecainide, levothyroxine, lithium, phenytoin, phenobarbital, rifampicin, theophylline, and warfarin.

In certain embodiments, the weight per volume (w/v) concentration of an API in predetermined liquid medications for use with syringes of the present disclosure is 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 20 µg/ml, 30 µg/ml, 40 µg/ml, 50 µg/ml, 60 µg/ml, 70 µg/ml, 80 µg/ml, 90 µg/ml, or 100 µg/ml. In certain embodiments, the weight per volume (w/v) concentration of an API in predetermined liquid medications for use with syringes of the present disclosure is 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, or 100 mg/ml.

In certain embodiments, each line increment of a graduated scale of API weight dosages closest in proximity axially on the barrel and further up the barrel away from the tip of the syringe than the prior line increment measures an API weight dosage that is incrementally greater than that measured by the last line increment 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 60 mg, 70 mg, 80 mg, 90 mg, or 1000 mg. In certain embodiments, each line increment of a graduated scale of API weight dosages closest in proximity axially on the barrel and further up the barrel away from the tip of the syringe than the prior line increment measures an API weight dosage that is incrementally greater than that measured by the last line increment by 1 µg, 2 µg, 3 µg, 4 µg, 5 µg, 6 µg, 7 µg, 8 µg, 9 µg, 10 µg, 15 µg, 20 µg, 25 µg, 30 µg, 35 µg, 40 µg, 45 µg, 50 µg, 60 µg, 70 µg, 80 µg, 90 µg, or 1000 µg. In certain embodiments, each line increment of a graduated scale of API weight dosages closest in proximity axially on the barrel and further up the barrel away from the tip of the syringe than the prior line increment measures an API weight dosage that is incrementally greater than that measured by the last line increment 1 pg, 2 pg, 3 pg, 4 pg, 5 pg, 6 pg, 7 pg, 8 pg, 9 pg, 10 pg, 15 pg, 20 pg, 25 pg, 30 pg, 35 pg, 40 pg, 45 pg, 50 pg, 60 pg, 70 pg, 80 pg, 90 pg, or 1000 pg. In certain embodiments, each line increment of a graduated scale of API weight dosages closest in proximity axially on the barrel and further up the barrel away from the tip of the syringe than the prior line increment measures an API weight dosage that is incrementally greater than that measured by the last line increment 1 fg, 2 fg, 3 fg, 4 fg, 5 fg, 6 fg, 7 fg, 8 fg, 9 fg, 10 fg, 15 fg, 20 fg, 25 fg, 30 fg, 35 fg, 40 fg, 45 fg, 50 fg, 60 fg, 70 fg, 80 fg, 90 fg, or 1000 fg.

In certain embodiments, the line increments of graduated scales of API weight dosages and/or the indicia of the identity of the API of the predetermined medication are comprised of ink printing, stamp printing, embossing, engraving, and/or etching and the like, either directly onto or inside of the barrel of the syringe, on a label affixed to the barrel, or a combination thereof. In certain embodiments, the line increments of each individual graduated scale of API weight dosages present on the barrel are of one color selected from red, orange, yellow, green, blue, indigo, violet, white, and black. In certain embodiments, the line increments of each individual graduated scale of API weight dosages present on the barrel are of one or more colors selected from red, orange, yellow, green, blue, indigo, violet, white, and black. In certain embodiments, a plurality of graduated scales of API weight dosages is present on the barrel, the line increments of each individual graduated scale of API weight dosages are of one color, and each of the graduated scales of API weight dosages is of a different color.

In certain embodiments, each individual marking of the two or more graduated scales of API weight dosages is labeled with the numerical weight dosage of the API measured thereby. In certain embodiments, the barrel is substantially free of any markings or printed, stamped, embossed, and/or etched lettering other than the aforementioned markings forming the graduated scales of API weight dosages, the numerical values of API weight dosages measured thereby, and optionally the name of the API. As used herein, the term "the barrel is substantially free of any markings or printed, stamped, embossed, and/or etched lettering" means that not less than 50%, 60%, 70%, 80%, 90%, 95%, 97.5% 99%, or 100% of a total surface area of the barrel that is not covered by the aforementioned markings forming the graduated scales of API weight dosages, the numerical values of API weight dosages measured thereby, and the name of the API divided by the total surface area of the barrel is free of any markings or printed, stamped, embossed, engraved, and/or etched lettering.

What is claimed is:

1. A syringe, calibrated for use with a predetermined liquid medication having a particular active pharmaceutical ingredient (API) at a particular weight per unit volume (w/v) concentration, the syringe comprising: a plunger and a barrel configured such that the plunger, or an end portion of the plunger, is sealingly receivable through an opening at one end of the barrel and within the barrel and slidingly moveable lengthwise within the barrel, which configuration forms a volumetrically adjustable reservoir inside the barrel into which only a single API weight dosage of the liquid medication is loaded through an intake opening for the liquid medication at the other end of the barrel,
wherein:
the barrel is made, in whole or in part, from substantially transparent material through which liquid medication inside the reservoir is visible;
the barrel comprises, extending along its lengthwise axis, two or more graduated scales of liquid medication API weight dosages on the substantially transparent material of the barrel, each of the two or more graduated scales occupying non-overlapping arcs running lengthwise along the circumference of the barrel;
each graduated scale is formed of a plurality of increment API weight dosage lines for the liquid medication, each increment line running perpendicular to the lengthwise axis of the barrel and immediately adjacent increment lines of any one graduated scale indicating API weight dosages that differ from each other by no more than 100 mg;
increment lines of one graduated scale are offset, along the lengthwise axis of the barrel, from increment lines of the other graduated scales;
at least every fifth increment line of any one graduated scale is labeled with the weight dosage of the API indicated thereby and such label is the only writing on the syringe unless the syringe is also marked with the name of the API, the medication, or both; and
the increment lines of all the graduated scales are arranged on the barrel in a manner such that, moving in a spiral fashion along the lengthwise axis of the barrel from any one increment line of a first graduated scale to another increment line of a second graduated scale that is closest in proximity to the one increment line, the one and the another increment lines indicate API weight dosages that differ front each other by no more than 50 mg.

2. The syringe of claim 1, wherein a maximum API weight dosage indicated by any graduated scale corresponds to a volume of the liquid medication loaded into the reservoir that is 1 ml, 2 ml, 3 ml, 5 ml, 10 ml, 15 mL, 20 ml, 25 ml, or 50 ml.

3. The syringe of claim 2, wherein each increment line and each increment line label is printed, stamped, embossed, engraved, and/or etched onto the barrel.

4. The syringe of claim 3, wherein the syringe is calibrated for use with the predetermined liquid medication having the particular API w/v concentration that that falls in a range of 1 mg/ml to 999 mg/ml.

5. The syringe of claim 4, wherein each immediately adjacent increment line of any one graduated scale indicate API weight dosages that differ from each other by no more than 90 mg, 80 mg, 70 mg, 60 mg, 50 mg, 40 mg, 30 mg, 20 mg, 15 mg, 10 mg, or 5 mg.

6. The syringe of claim 5, wherein the API has a narrow therapeutic index.

7. The syringe of claim 6, wherein the collection of increment lines of all the graduated scales are arranged on the barrel in a manner such that, moving in a spiral fashion along the lengthwise axis of the barrel from any one increment line of a first graduated scale to another increment line of a second graduated scale that is closest in proximity to the one increment line, the one and the another increment lines indicate API weight dosages that differ from each other by no more than 10 mg.

8. A syringe, calibrated for use with a predetermined liquid medication having a particular active pharmaceutical ingredient (API) at a particular weight per unit volume (w/v) concentration, the syringe comprising: a plunger and a barrel configured such that the plunger, or an end portion of the plunger, is sealingly receivable through an opening at one end of the barrel and within the barrel and slidingly moveable lengthwise within the barrel, which configuration forms a volumetrically adjustable reservoir inside the barrel into which only a single API weight dosage of the liquid medication is loaded through an intake opening for the liquid medication at the other end of the barrel, wherein:
the barrel is made, in whole or in part, from substantially transparent material through which liquid medication inside the reservoir is visible;
the barrel comprises, extending along its lengthwise axis, two or more graduated scales of liquid medication API weight dosages on the substantially transparent material of the barrel, each of the two or more graduated scales occupying non-overlapping arcs running lengthwise along the circumference of the barrel;
each graduated scale is formed of a plurality of increment API weight dosage lines for the liquid medication, each increment line running perpendicular to the lengthwise axis of the barrel and immediately adjacent increment lines of any one graduated scale indicating API weight dosages that differ from each other by no more than 100 ug;
increment lines of one graduated scale are offset, along the lengthwise axis of the barrel, from increment lines of the other graduated scales; and
at least every fifth increment line of any one graduated scale is labeled with the weight dosage of the API indicated thereby such label is the only writing on the syringe unless the syringe is also marked with the name of the API, the medication, or both; and
the increment lines of all the graduated scales are arranged on the barrel in a manner such that, moving in a spiral fashion along the lengthwise axis of the barrel from any one increment line of a first graduated scale to another increment line of a second graduated scale that is closest in proximity to the one increment line the one and the another increment lines indicate API weight dosages that differ from each other by no more than 50 ug.

9. The syringe of claim 8, wherein a maximum API weight dosage indicated by any graduated scale corresponds to a volume of the liquid medication loaded into the reservoir that is 1 ml, 2 ml, 3 ml, 5 ml, 10 ml, 15 mL, 20 ml, 25 ml, or 50 ml.

10. The syringe of claim 9, wherein each increment line and each increment line label is printed, stamped, embossed, engraved, and/or etched onto the barrel.

11. The syringe of claim 10, wherein the syringe is calibrated for use with the predetermined liquid medication having the particular API w/v concentration that falls in a range of 1 μg/ml to 999 μg/ml.

12. The syringe of claim 11 wherein each immediately adjacent increment line of any one graduated scale indicate API weight dosages that differ from each other by no more than 90 μg, 80 μg, 70 μg, 60 μg, 50 μg, 40 μg, 30 μg, 20 μg, 15 μg, 10 μg, or 5 μg.

13. The syringe of claim 12, wherein the API is levothyroxine or a pharmaceutically acceptable salt of levothyroxine.

14. The syringe of claim 13, wherein there are three graduated scales on the barrel, and wherein a maximum API weight dosage indicated by any graduated scale corresponds to a volume of the liquid medication loaded into the reservoir that is 3 ml or 5 ml.

15. The syringe of claim 14, wherein the graduated scales are calibrated for use with the predetermined liquid medication having the particular API w/v concentration that is 30 μg/ml or 50 μg/ml.

16. The syringe of claim 15, wherein immediately adjacent increment lines of any one graduated scale indicate levothyroxine or a physiologically acceptable salt thereof weight dosages that differ from each other by 15 μg or less.

17. A syringe, calibrated for use with a predetermined liquid medication having a particular active pharmaceutical ingredient (API) at a particular weight per unit volume (w/v) concentration, the syringe comprising: a plunger and a barrel configured such that the plunger, or an end portion of the plunger, is sealingly receivable through an opening at one end of the barrel and within the barrel and slidingly moveable lengthwise within the barrel, which configuration forms a volumetrically adjustable reservoir inside the barrel into which only a single API weight dosage of the liquid medication is loaded through an intake opening for the liquid medication at the other end of the barrel, wherein:

the barrel is made, in whole or in part, from substantially transparent material through which liquid medication inside the reservoir is visible;

the barrel comprises, extending along its lengthwise axis, three graduated scales of liquid medication API weight dosages on the substantially transparent material of the barrel, each of the three graduated scales occupying non-overlapping arcs running lengthwise along the circumference of the barrel;

each graduated scale is formed of a plurality of increment API weight dosage lines for the liquid medication, each increment line running perpendicular to the lengthwise axis of the barrel and immediately adjacent increment lines of any one graduated scale indicating API weight dosages that differ from each other by no more than 13 micrograms;

increment lines of one graduated scale are offset, along the lengthwise axis of the barrel, from increment lines of the other graduated scales; every increment line of any one graduated scale is labeled with the weight dosage of the API indicated thereby and such label is only writing on the syringe unless the syringe is also marked with the name of the API, the medication, or both; and the increment lines of all the graduated scales are arranged on the barrel in a manner such that, moving in a spiral fashion along the lengthwise axis of the barrel from any one increment line of a first graduated scale to another increment line of a second graduated scale that is closest in proximity to the one increment line, the one and the another increment lines indicate API weight dosages that differ from each other by not more than 50 ug.

* * * * *